(12) United States Patent
Exelmans

(10) Patent No.: US 9,597,048 B2
(45) Date of Patent: Mar. 21, 2017

(54) METHOD FOR SELECTING A DIRECT RADIOGRAPHIC PANEL AS ACTIVE DR PANEL

(71) Applicant: Agfa HealthCare NV, Mortsel (BE)

(72) Inventor: Walter Exelmans, Mortsel (BE)

(73) Assignee: AGFA HEALTHCARE NV, Mortsel (BE)

( * ) Notice: Subject to any disclaimer, the term of this patent is extended or adjusted under 35 U.S.C. 154(b) by 244 days.

(21) Appl. No.: 14/409,030

(22) PCT Filed: Jun. 28, 2013

(86) PCT No.: PCT/EP2013/063609
§ 371 (c)(1),
(2) Date: Dec. 18, 2014

(87) PCT Pub. No.: WO2014/005937
PCT Pub. Date: Jan. 9, 2014

(65) Prior Publication Data
US 2015/0177387 A1    Jun. 25, 2015

(30) Foreign Application Priority Data
Jul. 5, 2012  (BE) ................................ 2012/00460

(51) Int. Cl.
| | | |
|---|---|---|
| *H05G 1/56* | (2006.01) |
| *A61B 6/00* | (2006.01) |
| *G01T 1/17* | (2006.01) |
| *G06F 17/50* | (2006.01) |

(52) U.S. Cl.
CPC .......... *A61B 6/4494* (2013.01); *A61B 6/4216* (2013.01); *A61B 6/4233* (2013.01); *A61B 6/4452* (2013.01); *A61B 6/467* (2013.01); *A61B 6/542* (2013.01); *A61B 6/563* (2013.01); *A61B 6/587* (2013.01); *G01T 1/17* (2013.01); *G06F 17/50* (2013.01)

(58) Field of Classification Search
CPC ........... A61B 6/00; A61B 6/10; A61B 6/4208; A61B 6/4216; A61B 6/4266; A61B 6/542; A61B 6/563; A61B 6/58; A61B 6/581; A61B 6/587; G01T 1/17; H05G 1/56
USPC .......................................... 378/114, 116, 207
See application file for complete search history.

(56) References Cited

U.S. PATENT DOCUMENTS

| | | |
|---|---|---|
| 2010/0123083 A1 | 5/2010 | Petrick et al. |
| 2010/0169423 A1 | 7/2010 | Eguchi |
| 2011/0116486 A1 | 5/2011 | Tachikawa et al. |
| 2011/0274251 A1 | 11/2011 | Omernick et al. |
| 2011/0305319 A1 | 12/2011 | Liu et al. |

FOREIGN PATENT DOCUMENTS

EP    2 062 533 A1    5/2009

OTHER PUBLICATIONS

Official Communication issued in International Patent Application No. PCT/EP2013/063609, mailed on Sep. 26, 2013.
Exelmans, "Method for Controlling the Spatial Position of a Direct Digital X-Ray Detector", U.S. Appl. No. 14/409,035, filed Dec. 18, 2014.

*Primary Examiner* — Jurie Yun
(74) *Attorney, Agent, or Firm* — Keating and Bennett, LLP

(57) ABSTRACT

A method includes selecting, in a radiographic exposure unit, a direct radiographic panel as an active panel for a forthcoming radiographic exposure, activating a gravity sensor installed on the direct radiographic panel, and activating by the activated gravity sensor a processor installed on the direct radiographic panel. As a result of a communication from the processor with a radiographic work station over a network, the activated direct radiographic panel is retained as the active direct radiographic panel for the forthcoming radiographic exposure.

8 Claims, No Drawings

METHOD FOR SELECTING A DIRECT RADIOGRAPHIC PANEL AS ACTIVE DR PANEL

CROSS-REFERENCE TO RELATED APPLICATIONS

This application is a 371 National Stage Application of PCT/EP2013/063609, filed Jun. 28, 2013. This application claims the benefit of Belgian Patent Application No. 201200460, filed Jul. 5, 2012, which is incorporated by reference herein in its entirety.

BACKGROUND OF THE INVENTION

1. Field of the Invention

The present invention relates to a method for a convenient and operator-friendly selection of a direct radiographic panel as active DR Panel for a radiographic exposure.

2. Description of the Related Art

It is known that radiographic illumination or exposure has important applications in medical imaging, whereby the medical advantages for the patient largely exceed the small risk of damage resulting from such radiographic illumination.

In earlier days radiographic exposures mostly made use of film based on silver halide technology as image capturing medium.

Since a number of years the so-called computed radiography technique has gained wide market acceptance. This technology makes use of a radiographic panel that does not use silver halide technology as the light capturing medium, but uses stimulable phosphors.

This method is described amongst others in detail in the Handbook of Medical Imaging, (ed. R. V. Matter et al., SPIE Press, Bellingham, 2000).

During recent years, radiographic exposures increasingly make use of direct digital radiographic techniques, known as DR (Direct Radiography).

This method is increasingly used as alternative for film-based imaging techniques, as well as for the panels based on the use of stimulable phosphor-technologies, as described supra.

In this digital radiographic method the radiographic exposure energy is captured pixelwise in a radiographycally sensitive panel, and hereupon is converted to electronic image data by electronic components. Hereupon the information is read out imagewise and displayed on a suitable monitor for diagnostic purposes by a radiologist.

One of the driving forces behind the success of direct digital radiography is the ability to rapidly visualise the radiographic images and to efficiently and simply communicate over data networks to one or more sites for analysis and remote diagnosis by a radiologist or other medical expert. The delays that are characteristic for the development, packaging and physical transport of radiographic films are avoided by the above methods. Also the difficulties arising from the scanning of developed films and the corresponding loss in resolution is avoided by the above techniques.

The advantage of direct radiographic systems over computed radiographic systems, based on stimulable phosphors, is that no read-out (in a digitizer) of the latently captured radiographic image needs to take place. On the contrary, the digital radiographic image promptly or directly can be read for the purpose of evaluating the image from a diagnostic point of view. This diagnosis can take place at a local or remote workstation.

At the beginning the first direct radiographic panels were integrated in the overall radiographic imaging system. The wiring was designed such that minimal trouble to the radiographic operator was caused hereby when the radiographic direct panel was placed for exposure of a body part of a patient. More recently portable direct radiographic panels have been introduced to the market place. These panels make use of an on-board battery and communicate with the radiographic control panel or workstation, as well as with the data capturing apparatus and the display components in a wireless manner.

The latter aspects resulted in a wide acceptance of such portable wireless panels by the marketplace and ensures their practical use in a fully digital radiographic exposure system.

In a hospital or medical diagnosis center, these panels can be used as well in a completely newly installed radiographic imaging system or in a so-called retrofit situation. The term retrofit should be understood as directed to an existing radiographic system, that previously made use of radiographic films or stimulable phosphor plates, and whereby the latter registration media have been replaced by a direct radiographic capturing medium, a so-called direct radiographic or DR panel, without the need to replace the workstation or the radiographic source itself. The advantage of such a retrofit radiographic system as compared to a completely newly installed radiographic system, is its lower investment cost, as part of the already installed radiographic system can be re-used.

Although portability and wireless communication of the radiographic registration medium clearly is an advantage when portable and wireless DR panels are used, these features also are characterized by the occurrence of problems under practical circumstances of use. In particular such panels are characterized by identification or selection difficulties when they are used in a so-called multi-panel environment. This may lead to mistakes for example when resetting the correct panel, or the wrong use of a panel.

Contrary to radiographic films or stimulable phosphor panels that after exposure need to be removed from the radiographic exposure room for the purpose of being developed, resp. for being read-out in a digitizer, direct radiographic panels after use can remain in the radiographic exposure room.

When as a result of the above situation various direct radiographic panels are available in the radiographic exposure room, the radiographic operator needs to be fully sure that for the next or forthcoming radiographic exposure the right panel needs to be identified or selected.

Absent same it would be possible to address the wrong DR Panel, or to reset same, or the collect the data hereof.

Without a specific method that enables to reduce to an absolute minimum the probability of choosing a wrong DR Detector, there remains an enhanced risk for an incorrect exposure of a patient, resulting in retakes. On its turn, this results in a number of complaints, confusion, and a loss of time and efforts.

To cope with the above problems, Canon Inc., USA, has developed the following identification or selection method for direct radiographic panels, which it recommends for daily use. In the leaflet entitled 'Canon CXDI-70C Wireless Premium Flat Panel Detector', edited by Canon Medical Systems, A Division of Canon U.S.A. Inc., 15955 Alton Parkway, Irvine, Calif., USA, with reference DRB-014 Rev.

A, 0611/2000, website www.usa.canon.com/csdi-70cwireless, a method for the identification/selection of digital radiographic panels has been described.

(In the text that follows, both terms 'identification' or 'selection' of a direct radiographic panel is used, both terms having the same meaning.) The method described therein is as follows:

On the digital radiographic DR Canon Panels an infrared transmitter/sender is provided with pressure-sensitive button. This is the so-called IR check-in unit.

When a radiographic operator takes the Canon digital radiographic panel out of its docking station, he holds this panel on short distance before a radiographic workstation, wherein an infrared receiver is positioned.

Hereupon he pushes the IR pressure button, and the link to the radiographic workstation is unequivocally established.

As a result hereof the captioned direct radiographic panel is unambiguously and unmistakably identified and is ready for being used in the digital radiographic exposure unit.

During such identification the DR Panel receives the WIFI settings that are required to enable it to work in the setting of the radiographic workstation.

To this end, a fixed IP address, an SSID (Service Set Identifier) and a WPA-PSK (Wi-Fi Protected Access, Pre-Shared Key) of the access point and the IP address of the radiographic workstation is allocated to the DR Panel concerned.

The activation of the DR Panel as described above occurs in the Canon method by selecting the captioned panel on the workstation.

In US patent publication nr. US 2011/0116486 A1, published on May 19, 2011, in the name of Canon Kabushiki Kaisha, Tokyo, Japan, reference is made to the use of portable and wireless direct radiographic panels, and the identification of such panels by means of such infrared communication. For the purpose of identification of the DR Panel, 'an input unit is provided for the X-ray sensor apparatus and accepts input from the user'. (Paragraph 33) Further in paragraph 35 is stated that 'pressing the input unit of the X-ray sensor apparatus will start connection processing of the X-ray sensor apparatus to the access point.' The term 'pressing the input unit' is repeatedly used in this specification, see e.g. par. 41, 4° line, par. 47, 5° Line, par. 51, 2° line, par 55 last but one line, etc.

Upon pressing the input unit, the wireless communication starts, based on the use of IrDA, Transferjet or UWB (paragraph 33).

In European patent publication nr. EP 2 062 533 A1, published on May 27, 2009, in the name of Carestream Health, Inc., a method is also described for the identification, resp. the activation of direct radiographic panels. Hereby use is made of marking labels that are attached to the direct radiographic panels, whereby an operator, for example the radiologist or one of his assistants, activates the correct direct radiographic panel by means of the touch screen of the radiographic workstation.

This procedure however is also quite cumbersome: it implies that for each radiographic exposure the radiographic operator should go to the radiographic workstation, and there needs to navigate to the screen that shows the various possibly active DR Panels, and should then designate the correct panel by touching the correct field on the touch screen of the display.

In US Patent Application US 2010/0169423 A1, published Jul. 1, 2010, in the name of Konica Minolta Medical & Graphic, Inc, Tokyo, Japan, a radiographic image capturing systems is described, wherein a Flat Panel Detector (FPD) is activated and its IP address is communicated to the radiographic console, by means of pressing a pressure button by the radiographic operator. Reference is made to paragraph 58 stating that 'the operator depresses the button equipped on the FPD concerned . . . '

In US Patent Application US 2010/0123083 A1, published May 20, 2010, in the name of General Electric Company, NY, USA, an imaging system is provided, wherein the portable digital image detector may be configured to communicate its location to the system control circuitry. To that end, the digital detector may include various sensors and mechanisms configured to enable the system to determine the location of the detector (paragraph 28). The sensors may be mechanical sensors physically activated by engagement with actuators, or may include induction sensors triggered by proximity to the corresponding actuators.

Through such mechanism, the imaging system may detect the presence of a digital detector in e.g. its table or wall stand. Paragraph 31 discloses the use of a button or switch 'that may be engaged by a technician or other user'.

Apart from detecting the position of the digital detector, this specification discloses no other function associated with such actuators or sensors on the digital detector.

In US Patent Application US 2011/0274251 A1, published Nov. 10, 2011, in the name of General Electric Company, NY, USA, a method is described for coordinating operation of X-ray detectors in a wireless X-ray system, including detecting multiple wireless X-ray detectors within an operative range of an X-ray base station. Paragraph 24 of this specification discloses to this end the use of a button that may be pressed in response to instructions received from the X-ray base station to select the detector for registration.

In US Patent Application US 2011/0305319 A1, published Dec. 15, 2011, in the name of General Electric Company, NY, USA, a portable x-ray detector and a gravity sensor coupled thereto is described. A processor is coupled to the gravity sensor, programmed to receive an input from the gravity sensor, determine a physical orientation of the portable x-ray detector based on the received input, and generate an indication to reposition the portable x-ray detector. The aim of such gravity sensor and coupled processor is to solve the problem when the operator positions the x-ray detector out of alignment with respect to the x-ray source.

Apart from the above, this specification discloses no other function associated with such gravity sensor and its coupled processor.

The method as described above with the Canon detectors gives rise to problems under practical use: the method is quite cumbersome, and hence it occurs that this procedure is not applied, in particular in emergency situations. Same applies to the method described in the Carestream patent application, or to the methods described in the Konica & Minolta patent application, or any of the other cited patent publications.

On top hereof, these methods may well be suitable when one DR panel is in use in a given radiographic exposure room, but the method gives rise to problems when more DR panels simultaneously are available for use.

In a radiographic exposure room, in many cases various DR Detectors are used, as they differ for example in their respective sizes.

When a radiographic exposure is prepared from the central radiographic workstation or console, the correct panel should be selected for the forthcoming exposure. To this end an unambiguous link is required between the radiographic exposure as planned and the corresponding DR Panel.

As set forth supra, when the radiographic operator has selected the wrong DR Panel, the radiographic exposure cannot be effected correctly.

When the wrong panel is linked to the workstation, as soon as the exposure button has been activated, the wrong panel will start to integrate. This implies loss of image data.

SUMMARY OF THE INVENTION

Preferred embodiments of the present invention avoid the abovementioned problems by effecting an easy and unambiguous communication between the radiographic workstation and the DR Panel as selected by the radiographic operator for the forthcoming radiographic exposure. By such a correct communication, a wrongly selected DR Panel can be timely indicated at the workstation (this means, before the actual exposure takes place).

The abovementioned aspects are realised by the elements and method described below.

Specific features of preferred embodiments of the invention are also set forth below.

Further advantages and embodiments of the present invention are clarified in the description that follows.

DETAILED DESCRIPTION OF THE PREFERRED EMBODIMENTS

Preferred embodiments of the present invention relate to a method for identifying or selecting a direct radiographic panel as active panel in a forthcoming radiographic exposure, and to that end includes the following steps.

As a first step a gravity sensor, preferably a 3G sensor or accelerometer, that is provided or installed on the direct radiographic panel is activated by a radiographic operator.

Hereupon the activated sensor will in turn activate an electronic component such as a processor that is provided on the direct radiographic panel, whereby as a result of a communication of this component or processor with a radiographic work station over a network, the activated direct radiographic panel is retained as the active direct radiographic panel for the forthcoming radiographic exposure. The abovementioned electronic component or processor may consist of or comprise the communication module of the DR Panel as such.

According to a preferred embodiment the communication over the network occurs wirelessly, although the method of the present invention is equally beneficial in case a DR Detector is used that comprises a wired or tethered connection to the radiographic work station.

In case a wireless DR Detector is used, and its communication with the radiographic work station occurs over a wireless network, the electronic component or processor may consist of or comprise the wireless communication module of the DR Panel.

According to a preferred embodiment of the invention, prior to the radiographic exposure, a check has been effected by the operator as to the conformity of the direct radiographic panel selected according to the method described above with the (radiographic) worklist. Such worklist may be visualised on the work station after navigating through the medical care organisation's or hospital HIS or RIS system (HIS stands for Hospital Information System, RIS stands for Radiological Information System).

In a given radiographic exposure room, unit or department, a digital radiographic detector can only be connected to a single radiographic workstation at the time. As soon as one of the so connected DR panels has been caused to move by a radiographic operator, and its embedded or installed gravity-sensor has detected such movement, it will be identified as the active panel according to a method of the present invention.

This so identified or selected DR panel remains the 'active' panel for any forthcoming radiographic exposure. This situation does not change until another DR panel is moved by the radiographic operator and as a result hereof is identified as the 'active' panel.

As soon as a DR panel has been identified or selected as the 'active' panel according to a method of the present invention, according to a preferred embodiment of such invention, a conformity check is performed along the following lines.

Link to the HIS/RIS/Worklist:

According to a preferred embodiment of the present invention, after identification or selection of the direct radiographic panel according to a method of the present invention, the conformity of the so identified direct radiographic panel with the direct radiographic panel as set forth in the worklist of the radiographic work station for the forthcoming radiographic exposure is checked.

If the result of this conformity check is OK, the operator will proceed to the radiographic exposure.

According to a still further preferred embodiment, in case the conformity between the so identified direct radiographic panel and the direct radiographic panel as set forth in the worklist of the radiographic work station has not been established, a warning is given to the operator. Such warning may comprise a pop-up on the display of the radiographic workstation, optionally including an acoustic or other form of alarm.

In such a case, a manual intervention of the operator is required: he can either adapt the worklist by selecting another DR Panel for the forthcoming exposure, for example the DR Panel identified as the active panel, or alternatively, he may select the DR Panel set forth in the worklist, and identify such panel as the active DR Panel.

The DR panel which last was moved by the operator, and as a result hereof was identified as the active DR Panel for any forthcoming exposure, so remains the active panel for any further exposure, until another DR panel has been moved and consequently identified as the active DR panel.

According to a preferred embodiment, such newly identified DR panel shall only be accepted as the active DR Panel, after an positive conformity check with the radiographic worklist has been performed.

Once such new DR panel is indeed designated as the active DR Panel, it will on its turn keep such status, until another DR Panel is designated as the active DR Panel for forthcoming exposure(s).

The worklist of the planned radiographic exposures is usually displayed on the screen of the workstation during the various radiographic exposures that are planned for a given time-frame and for a given radiographic exposure room or unit.

Such worklist is part of or comprised within the Radiological Information System (RIS) of the hospital or medical care organisation and is communicated to the work station. Such communication may e.g. comprise the radiographic operator of the radiographic exposure unit concerned to navigate in the Hospital Information System (HIS) to the specific RIS data, and visualising on the screen or display of the radiographic work station such worklist. The radiographic worklist usually comprises one or more of the following information: identity of the patients to be radiographed (name or other personal attributes), object to be radiographed (arm, knee, hand, or other body part), stand (wall or bucky), as well as the digital radiographic panel to be used for the radiographic exposure, and—optionally—the exposure parameters.

Unique Identification of DR Panel:

Each direct radiographic panel has a unique identification number or other form of identification. Such identification is allocated to the panel at the time of manufacturing the panel or at the time of marketing of the direct radiographic panel.

The abovementioned unique identification code or number of the direct radiographic panel may comprise or consist of a unique serial- or manufacturing-number, or, in an alternate embodiment, may comprise or consist of the fixed or variable IP address, MAC address or some sort of Unique Identifier allocated to the DR Panel.

The electronic component or processor consists of or comprises, as set forth supra in case of a preferred embodiment of the invention, the (wireless) communication module of the direct radiographic panel. This communication module uses through the wireless communication protocol with the radiographic workstation this unique identification code to distinguish this DR Panel in an unambiguous manner from the other DR panels, and to identify same as such.

In a next step, namely after the radiographic exposure has taken place, the radiographic image data are sent to the radiographic workstation from the DR Panel that has been authenticated and registered to this end as the active DR Panel.

The authentification as active DR Panel takes place according to a method of the present invention.

The authentification as registered DR Panel can only take place when at the time of installment of the radiographic exposure room—or at the time of first use of the DR panel—the captioned DR Panel has been registered by its unique identification serial number or other form of identification by the radiographic workstation.

This is a typical administrative task that should not necessarily be performed by the radiologist, but can be taken care of by an administrative or technical assistant. Also the supplier or the approved or qualified installer of the radiographic exposure unit can take care hereof.

According to a method of the invention a gravity sensor, preferably a 3G-sensor or accelerometer, is incorporated in or on the direct radiographic panel. This sensor is in operative association with an electronic component or processor, that is equally well installed on the direct radiographic panel.

When the gravity sensor is activated, the sensor ensures that the electronic component or processor with whom it is operatively associated, is likewise activated. The latter then takes care of a (preferably wireless) data communication with the radiographic workstation, preferably by a WIFI or IEEE 802.11 network (a/b/g/n or the like).

The abovementioned electronic component may consist of or comprise the electronic chip for wireless communication with the radiographic workstation of the portable DR radiographic panel. It then suffices to electrically connect the gravity sensor with such electronic chip of the DR panel to realise the abovementioned operational association.

The processor or electronic chip that takes care of the wireless communication with the radiographic workstation, or the radiographic exposure unit, amongst others for the transmittal of the radiographic image data, is known to the person skilled in the art. Such module has been described e.g. in the U.S. patents of Fuji Photo Film, Inc., Japan, Nr. U.S. Pat. Nos. 7,829,859 and 8,116,599. The patent first mentioned describes how the portable DR Panel transmits the digital image data stored in the DR panel over such wireless communication panel to the radiographic console by a transceiver of the DR Panel. The UWB (Ultra Wide Band) protocol is mentioned as an example of such wireless communication. Such UWB Protocol is characterised by a substantial reduction of energy-consumption, and by enhanced communication speed, as compared to other wireless communication techniques.

The other U.S. patent, U.S. Pat. No. 8,116,599, describes the conversion to wireless communication signals of the image data by the wireless communication unit according to one of the following existing wireless communication protocols: UWB, Bluetooth, Zigbee, HiSWANa (High Speed Wireless Access Network type a), HiperLAN, Wireless 1394, Wireless USB, and finally Wireless LAN, infrared (irDA), NFC (Near Field Communication), IO-Homecontrol.

Preferably use is made of a wireless communication protocol working according to the IEEE 802.11 standard.

In such a case, the Direct Radiographic Panel communicates by a short-range radio or infrared connection over the wireless network with the radiographic workstation using any of the above communication protocols.

Generally a short-range radio connection is preferred over an infrared connection, as the first mentioned connection operates in an omnidirectional manner, whereas for an infrared connection, as it is an optical connection method, a direct optical path should be created between the transmitter and the receiver of the signals.

In a radiographic exposure room the various direct radiographic panels mostly are placed in their respective docking stations. The docking station is the place where the direct radiographic panel is positioned when it is not used for a radiographic exposure: through such docking station the DR Panel recharges its on-board battery.

A method according to the invention is however not limited hereto, but can also be applied when the non-active DR Panel, after it has been (re-)charged, is taken out of the docking station, and is positioned elsewhere in 'hold mode'.

As soon as the DR Panel is taken out of its docking station, or out of its 'hold mode' position, the gravity sensor provided on such panel will detect such movement occasioned by the radiographic operator. According to a method of this invention, this movement will then cause this panel to be used as active panel during a forthcoming radiographic exposure.

A gravity sensor is a sensor that detects the movement of an object, e.g. a direct radiographic panel, for example in case of removal of the panel out of the docking station.

A particularly preferred embodiment of such gravity sensor is a sensor that comprises an accelerometer, or a one- or three-dimensional (1-, 3-)g-sensor.

This is a small chip, wherein a minute mechanical element is incorporated.

An electric field keeps such element in its position, and in case of movement of the object whereupon such accelerometer is affixed, the chip registers the corresponding movement of the mechanical element, and consequently the object as a whole.

Such an element to a limited extent is comparable to the working principle of the gyroscopes of earlier days. Analog Devices is the name of a company that marketed the first digital accelerometers.

This kind of accelerometers are nowadays incorporated in smartphones to detect the position (vertically or horizontally), and to position the display accordingly. These components are equally well incorporated in other electronic devices such as iPad's, airbags, WII, etc.

The 1/3 g-sensors are in permanent electrical tension, and are charged by the on-board battery of the DR Panel.

Gravity sensors on the contrary are passive sensors: they hardly consume any electric current, and are charged by a node-battery; they may also be charged by the battery of the DR Panel.

In a further preferred embodiment of the present invention use is being made of (preferably three) 3-g sensors. This kind of sensors have the advantage that not only the movement of the direct radiographic panel whereupon they are affixed can be detected. As a result of the detection of the movement of the DR panel whereupon they are affixed, the DR panel can be marked as the active DR panel for the forthcoming radiographic exposure.

But these 3-g sensors also have the advantage that they can determine the relative position of the DR panel in a three-dimensional axis-system. As a result hereof, they can determine the position of the active DR panel, for example so as to check or control whether the active DR panel is positioned in the wall or the bucky of the radiographic exposure unit.

The latter enables the transmittal of a warning signal to the operator in case of an incorrect positioning of the active DR panel, before the actual radiographic exposure takes place.

Irrespective of the kind of sensor that is used, a gravity or a more specific accelerometer based sensor, as soon as such sensor is activated, it will on its turn activate the processor to which it is operatively associated. This processor will on its turn take care of the actual communication with the radiographic workstation. The sensor only detects that the radiographic panel whereupon it is affixed, is spatially moved, whereby such movement may imply that the detector is taken out of the docking station, or removed form its idle position by the radiographic operator. As soon as this step has occurred, the sensor on its turn will activate the electronic component, that is equally well affixed or incorporated in the direct radiographic panel.

Thus, once the sensor is activated, the processor in or at the activated direct radiographic panel will generate a signal in the wireless LAN network of the workstation, resulting in an unambiguous identification of this active direct radiographic panel on the basis of the abovementioned unique serial- or identification number or code, or alternatively by the IP address that is allocated to such panel.

The wireless LAN Network can make use of a number of various wireless network protocols and mechanisms. Preferably use is made of the wireless IEEE 802.11 g or IEEE 802.11 n interface (WIFI) standard.

One can also make use of the IEEE 802.11 b standard, whereby in a point-to-point configuration (1 point to various points), one access point (the wireless entry point) through a multidirectional antenna communicates with other clients that are within the range of the central access point.

The one access point is then the modality workstation, and the other clients are the various DR Panels, whereby one of these is identified/selected as the active panel.

So as to realise such wireless connection, preferably such WIFI connection, with the radiographic workstation, the processor has at its disposal on the direct radiographic panel an antenna driver and a chip technology that enables such short-range radio-connection.

To this end, the sensor as set forth supra, is operatively associated with such processor.

This operative association should be understood within the context of the present invention such that as soon as the sensor has been activated, an electronic signal is transmitted from such activated sensor to such processor, preferably including such antenna driver and chip, whereupon the latter is triggered to realise an effective communication with the workstation by the short-range radio network.

As soon as the latter has been realised, the captioned DR Panel is unambiguously identified by the workstation as the active DR Panel for the forthcoming radiographic exposure.

In the next step, once the radiographic exposure has taken place, the active DR panel will transmit its image data to the radiographic workstation, for visualisation and diagnostic evaluation on the monitor by a radiologist.

The invention claimed is:

1. A method for selecting in a radiographic exposure unit a direct radiographic panel as an active panel for a forthcoming radiographic exposure, the method comprising the steps of:
   activating a gravity sensor on the direct radiographic panel;
   activating a processor on the direct radiographic panel by using the activated gravity sensor to activate the direct radiographic panel; and
   causing the processor to communicate with a radiographic work station via a network; wherein
   as a result of the processor communicating with the radiographic work station, the activated direct radiographic panel is retained as the active panel for the forthcoming radiographic exposure.

2. The method according to claim 1, wherein the communication by the processor via the network with the radiographic work station occurs wirelessly.

3. The method according to claim 1, wherein the communication by the processor via the network with the radiographic workstation includes communicating a unique identification code of the activated direct radiographic panel.

4. The method according to claim 1, wherein after selection of the direct radiographic panel as the active panel and the radiographic exposure, a radiographic image stored in the activated direct radiographic panel is transmitted to the radiographic workstation.

5. The method according to claim 1, further comprising, after selection of the direct radiographic panel as the active panel, checking a conformity of the selected direct radiographic panel with a direct radiographic panel in a worklist of the radiographic work station for the forthcoming radiographic exposure.

6. The method according to claim 5, further comprising, in case the conformity between the selected direct radiographic panel and the direct radiographic panel in the worklist of the radiographic work station has not been established, providing a warning to an operator.

7. The method according to claim 1, wherein the gravity sensor includes one or more 1G-sensors or 3G-sensors.

8. The method according to claim 1, using the selected direct radiographic panel as the active panel for all forthcoming radiographic exposures until another direct radiographic panel has been selected as the active panel.

* * * * *